United States Patent [19]

Evans

[11] Patent Number: 5,777,131
[45] Date of Patent: Jul. 7, 1998

[54] POST MANUFACTURE PROCESS FOR IMPROVING THE PROPERTIES OF LACTONES AND SUBSTITUTED LACTAMS

[75] Inventor: Marshall Evans, Prairieville, La.

[73] Assignee: BASF Corporation, Mount Olive, N.J.

[21] Appl. No.: 696,700

[22] Filed: Aug. 14, 1996

Related U.S. Application Data

[63] Continuation-in-part of Ser. No. 562,232, Nov. 21, 1995, abandoned.

[51] Int. Cl.[6] .................. C07D 207/263; C07D 207/267
[52] U.S. Cl. ........................................... 548/543; 548/555
[58] Field of Search ........................... 548/541, 543, 548/555; 549/263, 295, 328

[56] References Cited

U.S. PATENT DOCUMENTS 3,969,344  7/1976  Ackermann et al. ............. 260/239.3 A
4,831,160  5/1989  Leighton .................................. 548/555

FOREIGN PATENT DOCUMENTS 2088850  6/1982  United Kingdom ............... 207/267

Primary Examiner—Johann Richter
Assistant Examiner—Jane C. Osweckí
Attorney, Agent, or Firm—Johanne P. Will

[57] ABSTRACT

This invention relates to a method for improving the properties of lactones and substituted lactams by subjecting the post-manufactured lactones and substituted lactams to an ion exchange resin. Specifically, this invention relates to a method for reducing the cationic impurities concentrations, reducing the amine concentration, and reducing the pH of post manufactured lactams.

9 Claims, 1 Drawing Sheet

POST MANUFACTURE PROCESS FOR IMPROVING THE PROPERTIES OF LACTONES AND SUBSTITUTED LACTAMS

This application is a continuation-in-part (CIP) of co-pending application Ser. No. 08/562,232, filed Nov. 21, 1995, now abandoned in favor of the present application.

BACKGROUND OF THE INVENTION

1. Field of the Invention

This invention relates to a method for improving the properties of lactones and substituted lactams, such as N-substituted-alpha-pyrrolidone, by subjecting the lactone or lactam to an ion exchange resin post-manufacture. Specifically, this invention relates to a method for reducing the cationic impurities, reducing the amine concentration, and lowering the pH of post-manufactured lactones and substituted lactams.

2. Background of the Invention

N-substituted-alpha-pyrrolidones (a substituted lactam), such as N-Methyl-2-Pyrrolidone (NMP) and lactones such as Gamma-Butyrolactone (GBL), are widely used in chemical syntheses as starting materials in chemical reactions, as polar solvents, in the production of electronic components, as cleaners and degreasers, and as an absorption media for the removal or separation of organic compounds from waste gases.

Specifically, NMP purity is important because many applications using NMP require low amine and cationic impurity concentrations and neutral pH. Amine concentration is an important characteristic of NMP with respect to the electrical properties and the corrosiveness of the amines in the NMP. Thus, reduction of amines is desired to enhance the electrical properties and reduce the corrosiveness of the amine component in the final NMP product. Cationic impurities concentrations are also an important characteristic of NMP with respect to the electrical properties of the cations in the NMP. Reduction of cationic impurities is desired because it improves the electrical properties of the final NMP product. The pH is also an important characteristic of NMP with respect to corrosiveness. Thus, a neutral pH solution (pH=7) is desired.

Currently, it is known in the art that amine concentrations, cationic impurities concentrations and pH can be controlled only in the processing stage of manufacturing via distillation. Also, U.S. Pat. No. 4,831,160, assigned to Exxon discloses a method for reducing the concentration of acidic components in NMP, used in extraction plants, comprising:

a) passing an NMP rich vapor stream to a sacrificial metal bed wherein the acidic component contaminants are removed from the NMP by conversion into metal salts of the acidic contaminants which, under a reflux of NMP, concentrate into a bottom fraction consisting of liquid NMP, the purified NMP being recovered as overhead vapor;

b) wherein said vapor NMP fraction contains organic acids resulting from the hydrolysis of a portion of the metal salts;

c) passing said NMP volatile acids fraction through a basic ion exchange resin bed wherein the acids are removed from the NMP, yielding a pure stream of NMP suitable for recycle.

Further, GB 2,088,850A, assigned to Coal Industry, Ltd., discloses a method of treating NMP to remove corrosive components comprising contacting the NMP with a basic ion exchange resin. Said method is particularly useful on-line in an aromatic hydrocarbon extraction plant.

However, the art does not disclose that treating lactones and substituted lactams post-manufacture with an ion exchange resin reduces the cationic impurities, reduces the amine concentration, and lowers the pH of post-manufactured lactones and substituted lactams. It has now been found that treating lactones and substituted lactams post-manufacture with an ion exchange resin significantly improves the properties of said lactones and substituted lactams.

SUMMARY OF THE INVENTION

A method for improving the properties of post-manufactured lactones and substituted lactams, such as N-substituted-alpha-pyrrolidone, comprising treating said post-manufactured lactones and substituted lactams with an ion exchange resin.

DETAILED DESCRIPTION OF THE INVENTION

Figure 1:
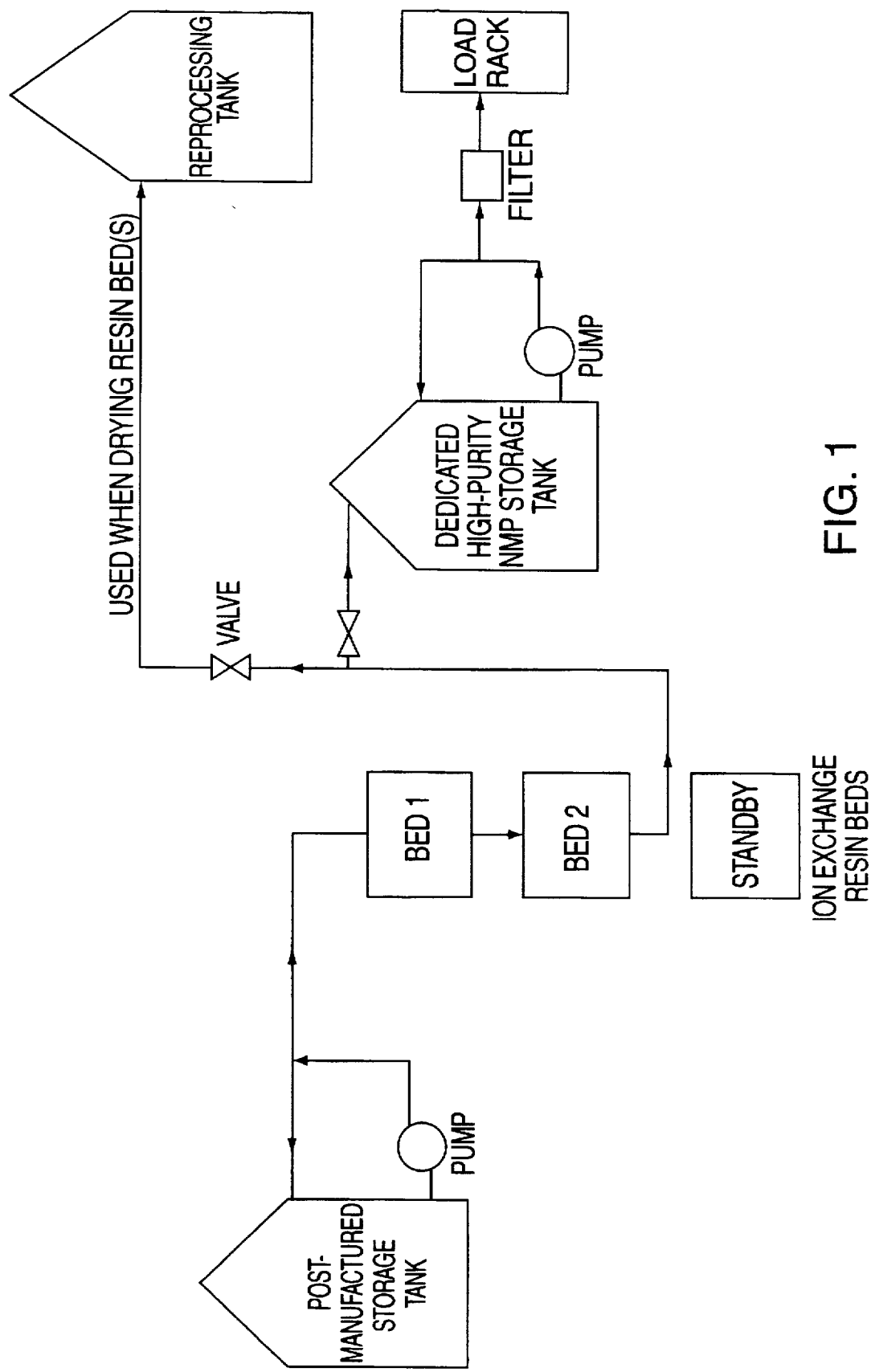
FIG. 1 illustrates the physical apparatus useful in practicing the present invention.

The present invention is a method of improving the properties of post-manufactured lactones and substituted lactams by subjecting said post-manufactured lactones and substituted lactams to treatment with an ion exchange resin. Lactones useful in the practice of the present invention, are formed by lactonization of various hydroxy acids to cyclic esters, such as gamma-butyrolactone. Examples of such lactones include, but are not limited to, lactones from aldonic acids and lactones from hydroxy acids, such as 2-methylene-gamma-butyrolactone, gamma-angelica lactone, 4-hydroxy-gamma-lactone, and gamma-caprolactone.

Substituted lactams useful in the practice of the present invention include, but are not limited to substituted lactams, such as the N-substituted-alpha-pyrrolidone group in this invention are N-methyl-α-pyrrolidone, N-ethyl-α-pyrrolidone, N-n-propyl-α-pyrrolidone, N-iso-propyl-αpyrrolidone, N-n-butyl-α-pyrrolidone, N-isobutyl-α-pyrrolidone, N-n-pentyl-α-pyrrolidone, N-n-hexyl-α-pyrrolidone, N-cycloalkyl-α-pyrrolidones like as N-cyclohexyl-α-pyrrolidone, N-chained alkyl-α-pyrrolidones like as N-n-decyl-α-pyrrolidone, and N-alkyl-α-pyrrolidone like as N-benzyl-α-pyrrolidone. Furthermore in these N-substituted-α-pyrrolidones substituting radicals of chain-alkyl, cyclo-alkyl and alal-alkyl can be replaced by Halogens, and —OH radicals.

The process of the present invention is particularly suitable for the post manufacture purification of NMP. NMP, $C_5H_9NO$, is the lactam of 4-methlaminobutyric acid. It has been found that when NMP samples are treated post-manufacture with an ion exchange resin there is a significant improvement in the quality of the final NMP product. Specifically, cationic impurities, including but not limited to, sodium, potassium, lithium, calcium and magnesium are reduced. Amine concentrations are reduced and pH is reduced from high basic values to "more neutral" and "completely neutralized" values. One skilled in the art understands "more neutral" to be a relative term. In other words, if the pH of recently post manufactured NMP is initially 11.5, a reduction in pH to 7.5 is "more neutral". The term "completely neutralized" represents, to one skilled in the art, a pH of 7. Thus, the post manufacture treatment of NMP with an ion exchange resin, according to the present invention, results in a reduction in the amine concentration from about 12 ppm to less than 1 ppm, a reduction in the cationic impurities concentration from about 100 ppb to less than 10 ppb, and a reduction in the pH from about 11.5 to 7.

In general, the ion exchange treatment of the post manufactured NMP is carried out for such a length of time as is effective for producing the desired reduction in the amine concentration, the cationic impurities concentration; and the pH value. The duration of the treatment will vary depending on the initial characteristics and size of the sample being treated. Further, one skilled in the art understands that the capability of the ion exchange resin to reduce the amine, cationic impurities and pH values depends on the age of the resin, the flow rate of the post manufactured NMP through the ion exchange resin, and the initial levels of impurities in the post manufactured NMP. In other words, fresh ion exchange resin provides optimum amine, cationic impurities and pH reduction capabilities.

The ion exchange resins useful in the practice of the present invention include, but are not limited to, cation exchange resins such as DOWEX® G23 and DOWEX® G26, DOWEX® HCR-S and DOWEX® HGR, available from the Dow Chemical Company, Midland, Mich.

Prior to treatment with ion exchange resins, post manufactured NMP typically has the properties as set forth in Table 1.

TABLE 1

| Typical Characteristics of Untreated, Commercially Available N-Methyl-2-Pyrrolidone | | | |
|---|---|---|---|
| Molecular Weight | 99.1 | sodium | 100 ppb |
| Refractive Index | 1.4700 | amine | 12 ppm |
| Boiling Point (760 mm $H_g$) | 397° F. | pH | 10.6 |
| Freezing Point (760 mm $H_g$) | −10.3° F. | | |
| Density (20° C.) | 1.93 gm/cc | | |

Treatment of the NMP, post-manufacture with an ion exchange resin will reduce the sodium concentration from 100 ppb to less than 10 ppb; the amine concentration from 12 ppm to less than 1 ppm; the pH from 10 to 7.

Prior to treatment with ion exchange resins, the post manufactured lactam N-Cyclohexyl-2-Pyrrolidone (CHP) typically has the properties as set forth in Table2.

TABLE 2

| Typical Characteristics of Untreated, Commercially Available N-Cyclohexyl-2-Pyrrolidone | | | |
|---|---|---|---|
| Molecular Weight | 167.2 | sodium | 100 ppb |
| Boiling Point (760 mmHg) | 290 Degrees C. | pH | 10.4 |
| Freezing Point (760 mm Hg) | 15–16 Degrees C. | | |
| Density (20 Degrees C.) | 1.03 gm/cc | | |

Treatment of CBP, post-manufacture with an ion exchange resin will reduce the sodium concentration from 100 ppb to less than 10 ppb; the ph from 10 to 7.

Prior to treatment with ion exchange resins, the post manufactured lactone, Gamma-Butyrolactone (GBL), typically has the properties as set forth in Table 3.

TABLE 3

| Typical Characteristics of Untreated, Commercially Available Gamma-Butyrolactone | | | |
|---|---|---|---|
| Molecular Weight | 86.1 | sodium | 30 ppb |
| Refractive Index | 1.4352 | pH | 5.2 |
| Boiling Point (760 mm Hg) | 206 Degees C. | | |
| Freezing Point (760 mm Hg) | −43.5 Degrees C. | | |
| Density (20 Degrees C.) | 1.13 gm/cc | | |

Treatment of the GBL, post-manufacture with ion exchange resin will reduce the sodium concentration from 30 ppb to less than 10 ppb.

Post-Manufacturing Purification of Lactones and Substituted Lactams by Ion-exchange Resin Treatment Process Description Those skilled in the art understand how to construct and operate an ion exchange resin apparatus. Further, individual manufacturing sites will construct and operate an ion exchange resin apparatus in ways best suited to their individual needs.

Basically, the purification of post manufactured lactones and substituted lactams according to the present invention, is carried out by passing post manufactured lactones and substituted lactams through an ion exchange resin apparatus. One skilled in the art understands that the configuration and number of ion exchange resin beds will vary according to the length and diameter of said resin beds. Preferably the ion exchange resin beds are cation exchangers, selected from DOWEX® G23 DOWEX® G26, DOWEX® HCR-S, and DOWEX® HGR. The ion exchange unit is fabricated with an integral spill collection pan draining to an extension of the plant trench system and from there to the wastewater treatment facility. Post manufactured lactones and substituted lactams are pumped, via a transfer pump, from a post manufacture storage tank. Product integrity is maintained during shipment by utilizing dedicated stainless steel (SS) loading lines, equipment, and transportation vessels.

As stated hereinbefore, each individual plant can set up an ion exchange resin system in any number of ways known to those skilled in the art.

Further, the flow rate of the post manufactured lactones and substituted lactams through the ion exchange resins is preferably about 0.5–100 gallons per minute (GPM); more preferably about 60–100 GPM; most preferably about 80–100 GPM Further, one skilled in the art understands that the slower the flow rate, the better the reduction of amines, cationic impurities, and pH will be. However, a slow flow rate will lengthen the treatment process. One skilled in the art understands that a balance must be achieved between speed and effectiveness. For example, a greater flow rate (80 GPM) through a new resin will provide the desired reduction in amines, cationic impurities, and pH. Further, a slower flow rate(0.5 GPM) through the same new resin will produce even greater reduction in amines, cationic impurities, and pH. Finally, a slower flow rate through an older resin will reduce impurities but the process will take longer. The flow rate of the post manufactured lactones and substituted lactams through the ion exchange resin bed(s) is established manually but monitored from a control room with a flow meter provided on the feed line. The ion exchange resin beds are switched at the first sign of breakthrough of the first bed. One skilled in the art understands "breakthrough" to be the point a which the undesired element is detected at above desirable levels; thus the resin must be replaced or refreshed.

Additionally, one skilled in the art understands that drying of new resin is required prior to its use in lactones and substituted lactams purification since the resin as supplied contains water. Field tests indicate that each resin bed requires approximately 350,000 lbs. of lactones and substituted lactams to dry the bed prior to use. A two inch carbon steel return line to the reprocessing tank is provided to allow drying of new beds at a low flow rate (limited by a restriction office). Each ion exchange resin bed is fitted with a Pressure Safety Valve (PSV)sized for the case of fire. Contamination of samples is avoided by enclosed sampling. The sampling system chosen is selected in concert with plant operations and quality assurance procedures, known to those skilled in the art.

Monitoring the Effectiveness of the Process

The following nonlimiting examples illustrate the effectiveness of the post-manufacturing ion exchange resin treatment process.

EXAMPLE 1

Pilot Plant Test

A pilot plant sample of NMP, said sample being approximately one pint in quantity, is treated with cation exchange resin. The sample is analyzed prior to treatment with the cation exchange resin and again after treatment with the cation exchange resin. Amine concentration and sodium concentration, are determined using standard testing methods according to Section 3.4 and 3.8.3 of the SEMI standard C 1.25, respectively, incorporated by reference herein. SEMI Standard method employ Inductively Coupled Plasma/ Atomic Emission Spectrophotometry (ICP/AES) in the analyses. The pH of a 50% solution is determined by ASTM D 1287, incorporated by reference herein.

The standard test results obtained from post-manufacture ion exchange treated NMP (Pilot Plant Test) are set forth in Table 4 below.

TABLE 4

Properties of N-Methyl-2-Pyrrolidone (NMP) Treated
Post-Manufacture with Ion Exchange Resin (DOWEX ® G 26)

|  | Prior to Ion Exchange Resin Treatment | After Ion Exchange Resin Treatment |
|---|---|---|
| pH, 50% Solution | 10.6 | 7.5 |
| Amines, ppm | 12 | less than 1 ppm |
| Sodium, ppb | 100 | less than 10 ppb |

EXAMPLE 2

Plant Test #1

1–4 Gallons Per Minute(GPM) of post manufactured NMP is run (predominantly 1 GPM) through 1 ft$^3$ of Dowex® G-26 resin. The first approximately 20,000 pounds of NWP treated has an average inlet (prior to treatment) amines by titration value of approximately 10 ppm. The average outlet (post treatment) amines concentration value is approximately 2 ppm. The average outlet (post treatment) amines concentration value for the entire 50,000 pound test is approximately 4 ppm. The average outlet sodium concentration is approximately 3 ppb which is well below the 10 ppb acceptable sodium level. All amine and sodium values are obtained according to the methods described in Section 3.4 and 3.8.3 of the SEMI Standard C 1.25, respectively. The pH value is reduced from 11.5 to 9.

EXAMPLE 3

Plant Test #2

0.5 GPM of post manufactured NMP is run through 1 ft$^3$ of Dowex® G-26 cation exchange resin. Approximately 100,000 pounds of NMP are treated. After some initial contamination, the inlet (prior to treatment) sodium value averaged approximately 19 ppb by ICP/AES and approximately 15 ppb by IC. The outlet (post treatment) concentration averages 1 ppb sodium by IC and essentially none is detected by ICP/AES. The inlet (prior to treatment) amine by titration values are 1–2 ppm with none detected in the outlet (post treatment). All amine and sodium values are obtained according to the methods obtained according to the methods described in Section 3.4 and 3.8.3 of the SEMI Standard C 1.25, respectively.

EXAMPLE 4

Pilot Plant Test

A pilot plant sample of N-Cyclohexyl-2-Pyrrolidone, CHP, said sample being approximately one pint in quantity, is treated with cation exchange resin. The sample is analyzed prior to treatment with the cation exchange resin and again after treatment with the cation exchange resin. Sodium concentration is determined using standard testing method according to 3.8.3 of the SEMI standard C 1.25, incorporated by reference herein. SEMI Standard method employ Inductively Coupled Plasma/Atomic Emission Spectrophotometiy (ICP/AES) in the analyses. The pH of a 50% solution is determined by ASTM D 1287, incorporated by reference herein.

The standard test results obtained from post-manufacture ion exchange treated CHP (Pilot Plant Test) are set forth in Table 5 below.

TABLE 5

Properties of N-Cyclohexyl-2-Pyrrolidone (CHP) Treated
Post-Manufacture with Ion Exchange Resin (DOWEX ® G 26)

|  | Prior to Ion Exchange Resin Treatment | After Ion Exchange Resin Treatment |
|---|---|---|
| pH, 50% Solution | 10 | 7 |
| Sodium, ppb | 100 | less than 10 ppb |

EXAMPLE 5

Pilot Plant Test

A pilot plant sample of Gamma-Butyrolactone, GBL, said sample being approximately one pint in quantity, is treated with cation exchange resin. The sample is analyzed prior to treatment with the cation exchange resin and again after treatment with the cation exchange resin. Sodium concentration is determined using standard testing method according to 3.8.3 of the SEMI standard C 1.25, incorporated by reference herein. SEMI Standard method employ Inductively Coupled Plasma/Atomic Emission Spectrophotometry (ICP/AES) in the analyses.

The standard test results obtained from post-manufacture ion exchange treated GBL (Pilot Plant Test) are set forth in Table 6 below.

TABLE 6

Properties of Gamma-Butyrolactone (GBL) Treated
Post-Manufacture with Ion Exchange Resin (DOWEX ® G 26)

|  | Prior to Ion Exchange Resin Treatment | After Ion Exchange Resin Treatment |
|---|---|---|
| Sodium, ppb | 30 | less than 10 ppb |

What is claimed is:

1. A method for improving the properties of post-manufactured substituted lactams selected from the group consisting of N-methyl-α-pyrrolidone, N-ethyl-α-pyrrolidone, N-n-propyl-α-pyrrolidone, N-iso-propyl-α-pyrrolidone, N-n-butyl-α-pyrrolidone, N-isobutyl-α-pyrrolidone, N-n-pentyl-α-pyrrolidone, N-n-hexyl-α-pyrrolidone, N-cycloalkyl-α-pyrrolidones N-chained alkyl-α-pyrrolidones and N-alkyl-α-pyrrolidone comprising treatment of said post-manufactured substituted lactams with an ion exchange resin.

2. A method according to claim 1 wherein said treatment is with a cation exchange resin.

3. A method according to claim 2 wherein said treatment with said cation exchange resin causes a reduction in the concentration of the amines present.

4. A method according to claim 2 wherein said treatment with said cation exchange resin causes a reduction of the pH.

5. A method according to claim 2 wherein said treatment with a cation exchange resin causes a reduction in the concentration of cationic impurities present.

6. A method according to claim 5 wherein said cationic impurity is sodium.

7. A method according to claim 3 wherein said reduction in the concentration of amines is from about 12 ppm to less than 1 ppm.

8. A method according to claim 4 wherein said reduction of pH is from about 11.5 to 7.

9. A method according to claim 6, wherein said reduction in the concentration of sodium is from about 100 ppb to less than 10 ppb.

* * * * *